United States Patent [19]

Kimura et al.

[11] Patent Number: 5,136,109
[45] Date of Patent: Aug. 4, 1992

[54] PROCESS FOR PREPARING 2,4-DICHLORO-3-ALKYL-6-NITRO-PHENOLS

[75] Inventors: Osamu Kimura, Sakai; Yasuhiko Horikawa, Kobe; Masaya Yamashita, Toyonaka; Kazutaka Morino, Osaka; Shinichi Koyama, Nara, all of Japan

[73] Assignee: Taoka Chemical Company, Ltd., Osaka, Japan

[21] Appl. No.: 707,097

[22] Filed: May 29, 1991

[30] Foreign Application Priority Data

Aug. 28, 1990 [JP] Japan ................... 2-227535
Aug. 30, 1990 [JP] Japan ................... 2-230040
Oct. 29, 1990 [JP] Japan ................... 2-293253
Oct. 29, 1990 [JP] Japan ................... 2-293254

[51] Int. Cl.$^5$ ............................................. C07C 205/26
[52] U.S. Cl. ................................. 568/709; 568/713
[58] Field of Search ................ 568/706, 709, 707, 713

[56] References Cited

U.S. PATENT DOCUMENTS

| | | | |
|---|---|---|---|
| 3,903,178 | 9/1975 | Nakamura et al. | 568/709 |
| 3,928,470 | 12/1975 | Soula et al. | 568/709 |
| 4,670,608 | 6/1987 | Paetz et al. | 568/709 |
| 4,731,320 | 3/1988 | Sasaki et al. | 430/505 |

FOREIGN PATENT DOCUMENTS

| | | | |
|---|---|---|---|
| 61-57536 | 3/1986 | Japan | 568/709 |
| 63-44552 | 2/1988 | Japan | 568/709 |
| 64-47741 | 2/1989 | Japan | 568/709 |
| 1-228943 | 9/1989 | Japan | 568/709 |
| 1-258649 | 10/1989 | Japan | 568/709 |
| 1361714 | 7/1974 | United Kingdom . | |

OTHER PUBLICATIONS

Patent Abstracts of Japan, Abstract No. 61-57536, vol. 10, No. 219, Jul. 31, 1986, p. 104 C 363.
Chemical Abstracts, vol. 100, No. 13, Mar. 26, 1984, p. 611 Abstract No. 102932f.
Chemical Abstracts, vol. 106, No. 5, Feb. 2, 1987, p. 503 Abstract No. 32565m.
Patent Abstracts of Japan, vol. 6, No. 139, Jul. 28, 1982, p. 139 C 116, abstract No. 57-64646.

*Primary Examiner*—Werren B. Lone
*Attorney, Agent, or Firm*—Birch, Stewart, Kolasch & Birch

[57] ABSTRACT

2-4-Dichloro-3-alkyl-6-nitrophenols which are useful as intermediate of cyan couplers in color photography are prepared by sulfonating 4-chloro-3-alkyl-phenols to obtain 5-chloro-4-alkylhydroxybenzenesulfonic acids, chlorinating the acids in an aqueous phase to obtain 3,5-dichloro-4-alkyl-2-hydroxybenzenesulfonic acids and nitrating the sulfonic acids.

21 Claims, No Drawings

PROCESS FOR PREPARING 2,4-DICHLORO-3-ALKYL-6-NITROPHENOLS

BACKGROUND OF THE INVENTION

1. Technical Field

The present invention relates to a process for preparing a 2,4-dichloro-3-alkyl-6-nitrophenol useful as intermediate of a cyan coupler in color photography.

2. Prior Art

As a process for preparing 2,4-dichloro-3-ethyl-6-nitrophenol, Japanese Patent Laid-Open Publication Nos. 44552/1988 and 47741/1989 disclose a method for obtaining it by nitrating 3,5-dichloro-4-ethylnitrobenzene to give 3,5-dichloro-4-ethyl-1,2-dinitrobenzene and hydrolyzing the nitro group at the 2-position of the dinitrobenzene with an alkali metal hydroxide.

Japanese Patent Laid-Open Publication No. 60634/1986 discloses a method for obtaining a 2,4-dichloro-3-alkyl-6-nitrophenol by chlorinating a p-alkylnitrobenzene with chlorine to give a 2,3,5-trichloro-4-alkylnitrobenzene, which is then subjected to hydrolysis.

Japanese Patent Laid-Open Publication No. 205447/1985 discloses a method for obtaining a 2,4-dichloro-3-ethyl-6-nitrobenzene by chlorinating 5-ethyl-2-nitrophenol with sulfuryl chloride in the presence of a catalyst.

Japanese Patent Laid-Open Publication No. 228943/1989 discloses a method for obtaining 2,4-dichloro-3-ethyl-6-nitrophenol by chlorinating p-ethylbenzenesulfonic acid to give 2,3,5-trichloro-4-ethylbenzenesulfonic acid, desulfonating and then nitrating the 2,3,6-trichloro-ethylbenzene obtained to give 2,3,5-trichloro-4-ethylnitrobenzene, and hydrolyzing a chlorine of the nitrobenzene.

Japanese Patent Laid-Open Publication No. 57536/1986 discloses a method for preparing 2,4-dichloro-3-ethyl-6-nitrophenol by sulfonating 4-chloro-3-ethylphenol or m-ethylphenol with a sulfonic anhydride complex in a halogenated hydrocarbon or with an excessive amount of concentrated sulfuric acid to give 5-chloro-4-ethyl-2-hydroxybenzenesulfonic acid or 4-ethyl-2-hydroxybenzenesulfonic acid and chlorinating the sulfonic acids with chlorine gas or sulfuryl chloride to form 3,5-dichloro-4-ethyl-2-hydroxybenzenesulfonic acid, of which the sulfonic group is then substituted by a nitro group with use of nitric acid.

All of the aforementioned well-known methods have various problems to be solved in order to practice them in industrial scale. For instance, in the method which uses 3,5-dichloro-4-ethyl-nitrobenzene as a starting material, difficulties are encountered in preparation of the starting compound. That is, nitration of ethylbenzene with use of mixed acid gives p-ethylnitrobenzene which is in the form of a mixture of ortho- and para-isomers.

Purification and separation of the p-isomer from the o-isomer is required and yield at this stage is not so high. Moreover, dichlorination of the p-ethylnitrobenzene accompanies undesirable isomers. Accordingly, complicated purification is actually required.

The method of trichlorination of p-ethylnitrobenzene also has the same defects as described above.

The method by using 5-ethyl-2-nitrophenol as a starting material is not practical by reason of the fact that it is difficult to prepare this starting material. That is, nitration of m-ethylphenol produces a mixture of isomers, and that it is required to remove by-products.

In the method with use of p-ethylbenzenesulfonic acid as a starting material, it is also required to separate the p-ethylbenzenesulfonic acid as a starting material from the o- or m-isomers on the preparation of the p-isomer. Such a method, in which chlorination is conducted in a large amount of sulfonic acid, has also problems such as a low volumetric efficiency or the treatment of sulfuric acid.

The method with use of m-ethylphenol as a starting material is not preferred, since it produces isomers in the sulfonation of the m-ethylphenol, so that it gives a low yield. The method, in which 4-chloro-3-ethylphenol is sulfonated with a sulfuric anhydride complex, has problems that special care is required because of the danger in handling of sulfuric anhydride. In addition, a raw material such as dioxane, which is required for the formation of the complex, is difficult to be recovered.

The method, in which 4-chloro-3-ethylphenol is sulfonated by concentrated sulfuric acid, also has problems on its industrialization. That is, volumertic efficiency is low due to the necessity of concentrated sulfuric acid in an excessive amount up to 5-7 moles to the amount of the ethylphenol and the treatment operation of sulfuric acid is difficult.

The method of chlorination with chlorine gas or sulfuryl chloride is disadvantageous for the practice in an industrial scale. When chlorine gas is used, a special safety device is required because of its nature. When sulfuryl chloride is used, the reagent is expensive and the reaction is required to be conducted in an organic solvent.

The present invention provides an industrially advantageous method for preparing a 2,4-dichloro-3-alkyl-6-nitrophenol as a final object, which has fewer problems described above.

SUMMARY OF THE INVENTION

The present invention is a process for preparing a 2,4-dichloro-3-$C_1$-$C_4$-alkyl-6-nitrophenol, comprising sulfonating a 4-chloro-3-$C_1$-$C_4$-alkylphenol with a sulfonating agent to give a 5-chloro-4-$C_1$-$C_4$-alkyl-2-hydroxybenzenesulfonic acid, chlorinating the sulfonic acid with hydrochloric acid and hydrogen peroxide in the presence or absence of a catalyst to form a 3,5-dichloro-4-$C_1$-$C_4$-alkyl-2-hydroxybenzenesulfonic acid, and substituting the sulfonic acid group in the sulfonic acid by a nitro group with nitric acid.

The process according to the present invention is described in detail below.

The process according to the present invention, as described above, is a process for preparing a 2,4-dichloro-3-$C_1$-$C_4$-alkyl-6-nitrophenol, comprising using a 4-chloro-3-alkylphenol as a starting material, which is subjected to three step reactions of sulfonation, chlorination and nitration. Particularly, the process according to the present invention is featured in a process for preparing a 2,4-dichloro-3-$C_1$-$C_4$-alkyl-6-nitrophenol by the chlorination step.

As hydrochloric acid used for the chlorination of the present invention, the industrially available one in the form of a hydrochloric acid solution (5-38%) is most preferably used. It may also be a gaseous hydrogen chloride which is ordinarily used in the technical field of chlorination reaction, and the gaseous hydrogen chloride is introduced into a reaction mixture via a suitable distributor.

Hydrogen chloride is used in a proportion of 0.9 mole or more, preferably 1–10 moles, more preferably 1–4.0 moles to mole of a 5-chloro-4-$C_1$-$C_4$-alkyl-2-hydroxybenzenesulfonic acid.

As the hydrogen peroxide used in the present invention, the one in the form of an aqueous solution of hydrogen peroxide (5–60%) is most preferably used. It is also possible to use hydrogen peroxide having a high concentration of $H_2O_2$ such as 98% $H_2O_2$.

Hydrogen peroxide is usually used in a stoichiometric amount to the aforementioned hydrogen chloride, but it is used preferably in a slightly excessive amount. Thus, the amount of hydrogen peroxide used is in the range of 0.5–2 moles, preferably 1–1.2 moles to 1 moles of hydrogen chloride.

In the chlorination of the present invention, a catalyst can be used. The catalyst used specifically includes aluminium chloride, ferric chloride or the like.

The amount of the catalyst used in in the range of 0.1–10% by weight, preferably 0.1–3% by weight to 5-chloro-4-$C_1$-$C_4$-alkyl-2-hydroxybenzenesulfonic acid.

The optical reaction temperature of chlorination depends on the non-aqueous or aqueous phase and is generally in the range of 80° C. or less, preferably 60° C. or less. In the case of the non-aqueous phase, the reaction is conducted at a temperature in the range of 50° C. or less, preferably in the range of about 10°–40° C.

The reaction mixture is diluted with water to give 3,5-dichloro-4-$C_1$-$C_4$-alkyl-6-hydroxybenzenesulfonic acid as an aqueous solution. Most impurities are extracted and removed into an oil layer.

The chlorination reaction of the present invention is particularly excellent industrially in that it can be conducted in the presence of water as a solvent.

In the process of the present invention, the step of sulfonation is not limitative and includes a sulfonation method of a 4-chloro-3-$C_1$-$C_4$-alkylphenol with a sulfuric anhydride complex, a sulfonation method with sulfuric acid or a sulfonation method with chlorosulfonic acid in an organic solvent.

However, the present inventors have found that the sulfonation method with chlorosulfonic acid in an organic solvent is most preferred in industry.

In this connection, the chlorosulfonic acid used herein generally has a purity in the range of 95–99.5%.

The amount of chlorosulfonic acid used is, for example, in a proportion of 0.9–1.4 moles, preferably 0.95–1.20 moles to a 4-chloro-3-$C_1$-$C_4$-alkylphenol. It is also sufficient that the amount is in a proportion of less than 0.9 mole or more than 1.4 moles. However, if the amount is too small, an amount of the unaltered 4-chloro-3-$C_1$-$C_4$-alkylphenol is increased. When the amount is too large, amounts of by-products are increased.

As the organic solvent in the sulfonation of the present invention, there are used halogenated hydrocarbons such as methylene chloride, chloroform, carbon tetrachloride, dichloroethylene, dichloroethane, trichloroethylene, trichloroethane, tetrachloroethylene, tetrachloroethane, dibromoethane, chlorobenzene, o-dichlorobenzene or the like; nitrated hydrocarbons such as nitrobenzene, o-nitrotoluene or the like; or aromatic hydrocarbons such as toluene, xylene, t-butylbenzene or the like.

The sulfonation reaction with chlorosulfonic acid is advantageously conducted at a temperature in the range of 0°–80° C., preferably 10°–50° C.

The 5-chloro-4-$C_1$-$C_4$-alkyl-2-hydroxybenzenesulfonic acid thus obtained is chlorinated to give a 3,5-dichloro-4-$C_1$-$C_4$-alkyl-2-hydroxybenzenesulfonic acid.

The chlorination is conducted by flowing chlorine gas or with sulfuryl chloride (non-aqueous system). Alternatively, the chlorination is effected with hydrogen chloride and hydrogen peroxide (aqueous system). The present inventors have found that the latter method, i.e. aqueous system method, is most preferred industrially.

The chlorination reaction of the present invention is particularly excellent industrially, since the reaction can be conducted in the presence of water as a solvent. The reaction is advantageous in that, in the case of a sulfonation method with chlorosulfonic acid, the reaction mixture is poured into water after the reaction is over, and then the aqueous layer is employed for the chlorination in an aqueous solvent without isolation of the sulfonic acid.

The 3,5-dichloro-4-$C_1$-$C_4$-alkyl-2-hydroxybenzenesulfonic acid is nitrated with nitric acid to give a 2,4-dichloro-3-$C_1$-$C_4$-alkyl-6-nitrophenol. Substitution of a sulfonic acid group of the sulfonic acid with a nitro group is effected.

As the nitration reaction, there is a method for substituting the sulfonic acid group with a nitro group by adding dropwise nitric acid to the aqueous solution of a 3,5-dichloro-4-$C_1$-$C_4$-alkyl-2-hydroxybenzenesulfonic acid obtained by the chlorination reaction. Alternatively, an aqueous solution of a 3,5-dichloro-4-$C_1$-$C_4$-alkyl-2-hydroxybenzene-sulfonic acid may be added dropwise to an aqueous nitric acid solution. However, the present inventors have found that the yield of nitration is remarkably increased by the latter method, that is, adding dropwise the aqueous solution of a 3,5-dichloro-4-$C_1$-$C_4$-alkyl-2-hydroxybenzenesulfonic acid to an aqueous nitric acid solution.

It is advantageous to conduct the nitration reaction at a temperature of 80° C. or less; particularly at 60° C. or less.

The aimed product, 2,4-dichloro-3-$C_1$-$C_4$-alkyl-6-nitrophenol is obtained by filtration of crystalline products after the nitration reaction is over. If necessary, water-soluble impurities are removed by extraction with an aromatic hydrocarbon such as benzene, toluene, xylene, monochlorobenzene, orthodichlorobenzene or the like, prior to the filtration. Alternatively, the extraction may be made with a chlorinated hydrocarbon such as chloroform, methylenechloride, dichloroethane, trichloroethane or the like. It is also possible to conduct washing or recrystallization with methanol, isopropanol or the like.

While the concentration of nitric acid used in the present invention is not particularly limited, the nitric acid is preferably used in the form of an aqueous solution having a concentration in the range of 2–70% by weight.

The amount of nitric acid used is in a proportion of 0.9 mole or more, preferably in the range of 1–10 moles, more preferably 1–4 moles to 1 mole of a 3,5-dichloro-4-$C_1$-$C_4$-alkyl-2-hydroxybenzenesulfonic acid.

The nitration reaction of the present invention is conducted generally at a temperature of 80° C. or less, preferably 60° C. or less, more preferably 40° C. or less.

In preparation of a 2-nitro-4,6-dicloro-5-$C_1$-$C_4$-alkylphenol by substituting a sulfonic acid group of a 3,5-dichloro-4-$C_1$-$C_4$-alkyl-2-hydroxybenzenesulfonic acid with a nitro group by use of nitric acid, a method of dropwise adding nitric acid to a 3,5-dichloro-4-$C_1$-$C_4$-alkyl-2-hydroxybenzenesulfonic acid has a problem that an inductive period from starting the dropwise addition of nitric acid until the initiation of the reaction is long. It is necessary to increase the added amount of nitric acid or to raise the reaction temperature for shortening the inductive period. However, if the amount of nitric acid added dropwise is increased, the reaction starts with a too large exotherm to control the temperature, and thus the reaction is too hard to be practiced in an industrial scale. If the reaction temperature is raised, impurities other than the aimed product 2,4-dichloro-3-$C_1$-$C_4$-alkyl-6-nitrophenol, such as dinitro derivatives, tend to be so easily produced that the method is inconvenient in view of its quality and yield.

According to the present invention, the preparation of 2,4-dichloro-3-ethyl-6-nitrophenol by nitration of an aqueous solution of a 3,5-dichloro-4-$C_1$-$C_4$-alkyl-2-hydroxybenzenesulfonic acid with an aqueous nitric acid solution is conducted with great safety and with high yield. The inductive period is greatly shortened by reuse of a filtrate obtained by filtration or separation of the resulting 2,4-dichloro-3-$C_1$-$C_4$-alkyl-6-nitrophenol after the nitration reaction or a supernatant of the solution, as a part or the whole of a solvent in the nitration reaction between the aforementioned 3,5-dichloro-4-$C_1$-$C_4$-alkyl-2-hydroxybenzenesulfonic acid and nitric acid.

In the nitration reaction of the present invention, the filtrate or the aqueous layer reused may be contained in either the aqueous nitric acid solution or an aqueous 3,4-dichloro-4-$C_1$-$C_4$-alkylhydroxybenzene solution, or both.

The amount of nitric acid used in the present invention is in a proportion of 0.9 mole or more, preferably 1–10 moles, more preferably 1–4.0 moles of the total of a newly charged aqueous nitric acid solution and the nitric acid contained in the filtrate or the aqueous layer to 1 mole of a 3,5-dichloro-4-$C_1$-$C_4$-alkyl-2-hydroxybenzenesulfonic acid.

EFFECT OF THE INVENTION

According to the process of the present invention, the aimed product of a 2,4-dichloro-3-$C_1$-$C_4$-alkylethyl-6-nitrophenol is prepared safely with a high purity and a high yield by starting from a 4-chloro-3-$C_1$-$C_4$-alkylphenol through a 5-chloro-4-$C_1$-$C_4$-alkyl-2-hydroxybenzenesulfonic acid and a 3,5-dichloro-4-$C_1$-$C_4$-alkyl-2-hydroxybenzenesulfonic acid.

EXAMPLE

The present invention is further explained in detail below with reference to Examples, but it is not limited to Examples.

EXAMPLE 1

In a 1-liter four-necked glass flask is prepared a solution mixture of 100 g of 4-chloro-3-ethylphenol and 350 g of dichloroethane. While the mixture is maintained at a temperature of 35°–45° C., 80 g of chlorosulfonic acid is added dropwise and the mixture is maintained at a temperature of 40°–45° C. for 1 hour. Next, 326 g of a 14.3% hydrochloric acid solution is added, and 68 g of a 35% aqueous hydrogen peroxide solution is added dropwise while maintaining the temperature at 40°–45° C. After the mixture is maintained at the same temperature for 8 hours, it is cooled to 20° C. After the oily layer is separated, the aqueous layer is placed in a dropping funnel and added dropwise, at 30°–40° C., to 230 g of a 35% aqueous nitric acid solution which has been preliminarily charged in a 1-liter four-necked glass flask. The liquid becomes turbid and turns yellowish white and the reaction is initiated. After the addition is over, the reaction mixture is maintained at the same temperature for 2 hours. The reaction mixture is cooled to 5° C. and filtered. The product is washed with water and dried to give 2,4-dichloro-3-ethyl-6-nitrophenol.

Yield, 143 g (95% yield based on 4-chloro-3-ethylphenol),

Purity, 99.2% (percentage based on LC area).

EXAMPLE 2

In a 500 ml four-necked glass flask is prepared a solution mixture of 100 g of 4-chloro-3-ethylphenol and 200 g of monochlorobenzene. While the mixture is maintained at a temperature of 25°–30° C., 80 g of chlorosulfonic acid is added dropwise. After the mixture is maintained at the same temperature for 3 hours, it is discharged in a 1-liter four-necked glass flask in which 200 g of water has been charged.

Next, 133 g of a 35% hydrochloric acid solution is added, and 93 g of a 35% aqueous hydrogen peroxide solution is added dropwise while maintaining the temperature at 30° C. After the mixture is maintained at the same temperature for 3 hours, it is cooled to 20° C. After the oily layer is separated, 319 g of a 70% aqueous nitric acid solution is added dropwise to the aqueous layer while keeping the temperature at 20°–25° C. After the addition is completed, the mixture is heated to 45° C. and maintained at the temperature for 4 hours. The reaction mixture is cooled to 5° C. and filtered. The product is washed with water and dried to give 2,4-dichloro-3-ethyl-6-nitrophenol.

Yield, 134.5 g (89% yield based on 4-chloro-3-ethylphenol).

EXAMPLE 3

Reaction was conducted in the same manner as in Example 2 except that 1.3 g of aluminium chloride is used as a catalyst of chlorination. As a result, 136.0 g of 2,4-dichloro-3-ethyl-6-nitrophenol is obtained (yield, 90%).

EXAMPLE 4

In a 500 ml four-necked glass flask is prepared a solution mixture of 100 g of 4-chloro-3-ethylphenol and 200 g of monochlorobenzene. While the mixture is maintained at a temperature of 25°–30° C., 80 g of chlorosulfonic acid is added dropwise. After the mixture is maintained at the same temperature for 3 hours, it is discharged in a 1-liter four-necked glass flask in which 200 g of water has been charged.

After the oily layer is separated, 133 g of a 35% hydrochloric acid solution is added to the aqueous layer and 93 g of a 35% aqueous hydrogen peroxide solution is added dropwise to the aqueous layer while keeping the temperature at 30° C. After the mixture is maintained at the temperature for 3 hours, the reaction mixture is cooled to 20° C. To the mixture is added dropwise 319 g of a 70% aqueous nitric acid solution with maintaining the temperature at 20°–25° C. After the addition is completed, the mixture is heated to 45° C. and maintained at the temperature for 4 hours. The reaction mixture is cooled to 5° C. and filtered. The product is washed with water and dried to give 2,4-dichloro-3-ethyl-6-nitrophenol.

Yield, 128.4 g (85% yield based on 4-chloro-3-ethylphenol).

EXAMPLE 5

In a 500 ml four-necked glass flask is prepared a solution mixture of 100 g of 4-chloro-3-ethylphenol and 350 g of dichloroethane. While the mixture is maintained at a temperature of 25°–30° C., 80 g of chlorosulfonic acid is added dropwise. After the mixture is maintained at the same temperature for 3 hours, it is discharged in a 1-liter four-necked glass flask in which 200 g of water has been charged.

Next, 133 g of a 35% hydrochloric acid solution and 1.3 g of aluminium chloride are added, and then 181 g of a 18% aqueous hydrogen peroxide solution is added dropwise while maintaining the temperature at 30° C. After the mixture is maintained at the temperature, it is cooled to 20° C. After the oily layer is separated, 319 g of a 70% aqueous nitric acid solution is added dropwise to the aqueous layer while keeping the temperature at 30° C. After the addition is completed, the mixture is heated to 45° C. and maintained at the temperature for 4 hours. The reaction mixture is cooled to 5° C. and filtered. The product is washed with water and dried to give 2,4-dichloro-3-ethyl-6-nitrophenol.

Yield, 126.8 g (84% yield based on 4-chloro-3-ethylphenol).

EXAMPLE 6

In a 1-liter four-necked glass flask is prepared a solution mixture of 100 g of 4-chloro-3-ethylphenol and 350 g of dichloroethane. While the mixture is maintained at a temperature of 35°–45° C., 80 g of chlorosulfonic acid is added dropwise and the mixture is maintained at a temperature of 40°–45° C. for 1 hour. Next, 326 g of a 14.3% hydrochloric acid solution is added, and 68 g of a 35% aqueous hydrogen peroxide solution is added dropwise while maintaining the temperature at 40°–45° C. After the mixture is maintained at the same temperature for 8 hours, it is cooled to 20° C. After the oily layer is separated, the aqueous layer is placed in a dropping funnel and added dropwise at 30°–40° C. to 172.5 g of a 70% aqueous nitric acid solution which has been preliminarily charged in a 1-liter four-necked glass flask. The liquid becomes turbid and turns yellowish white as soon as the addition is initiated. After the addition is over, the reaction mixture is maintained at the same temperature for 2 hours. The reaction mixture is cooled to 5° C. and filtered. The product is washed with water and dried to give 2,4-dichloro-3-ethyl-6-nitrophenol.

Yield, 143 g (92% yield based on 4-chloro-3-ethylphenol),

Purity, 99.0% (percentage based on LC area).

EXAMPLE 7

In a 1-liter four-necked glass flask is prepared a solution mixture of 100 g of 4-chloro-3-ethylphenol and 350 g of dichloroethane. While the mixture is maintained at a temperature of 35°–45° C., 80 g of chlorosulfonic acid is added dropwise and the mixture is maintained at a temperature of 40°–45° C. for 1 hour. Next, 326 g of a 14.3% hydrochloric acid solution is added, and 68 g of a 35% aqueous hydrogen peroxide solution is added dropwise while maintaining the temperature at 40°–45° C. After the mixture is maintained at the same temperature for 8 hours, it is cooled to 20° C. After the oily layer is separated, the aqueous layer is placed in a dropping funnel and added dropwise to 230 g of a 35% aqueous nitric acid solution which has been preliminarily charged in a 1-liter four-necked glass flask and maintained at a temperature of 30°–40° C. The liquid becomes turbid and turns yellowish white as soon as the addition is initiated. After the addition is over, the reaction mixture is further maintained at the same temperature for 3 hours. The reaction mixture is cooled to 5° C. and filtered. The filtrate (A) is obtained in an amount of about 650 g. The cake is washed with water and dried to give 2,4-dichloro-3-ethyl-6-nitrophenol.

Yield, 142 g (94% yield based on 4-chloro-3-ethylphenol),

Purity, 99.1% (percentage based on LC area).

On the other hand, in a 1-liter four-necked glass flask is prepared a solution mixture of 100 g of 4-chloro-3-ethylphenol and 350 g of dichloroethane. While the mixture is maintained at a temperature of 35°–40° C., 80 g of chlorosulfonic acid is added dropwise and the mixture is maintained at a temperature of 40°–45° C. for 1 hour. Next, 326 g of a 14.3% hydrochloric acid solution is added, and 68 g of a 35% aqueous hydrogen peroxide solution is added dropwise while maintaining the temperature at 40°–45° C. After the mixture is maintained at the same temperature for 8 hours, it is cooled to 20° C. After the oily layer is separated, the aqueous layer is placed in a dropping funnel and added dropwise to 115 g of a 70% aqueous nitric acid solution and a 115 g portion of the filtrate (A) obtained by the aforementioned manner which have been preliminarily charged in a 1-liter four-necked glass flask and maintained at a temperature of 20°–30° C. The liquid becomes turbid and turns yellowish white as soon as the addition is initiated. After the addition is over, the reaction mixture is further maintained at the same temperature for 3 hours. The reaction mixture is cooled to 5° C. and filtered. The filtrate (B) is obtained in an amount of about 650 g. The product is washed with water and dried to give 2,4-dichloro-3-ethyl-6-nitrophenol.

Yield, 145 g (96% yield based on 4-chloro-3-ethylphenol),

Purity, 99.8% (percentage based on LC area).

EXAMPLE 8

In a 1-liter four-necked glass flask is prepared a solution mixture of 100 g of 4-chloro-3-ethylphenol and 350 g of dichloroethane. While the mixture is maintained at a temperature of 35°–45° C., 80 g of chlorosulfonic acid is added dropwise and the mixture is maintained at a temperature of 40°–45° C. for 1 hour. Next, 326 g of a 14.3% hydrochloric acid solution is added, and 68 g of a 35% aqueous hydrogen peroxide solution is added dropwise while maintaining the temperature at 40°–45° C. After the mixture is maintained at the same temperature for 8 hours, it is cooled to 20° C. After the oily layer is separated, the aqueous layer obtained is charged in a 2-liter four-necked glass flask. A 460 g portion of the filtrate (A) obtained in the nitration reaction in Example 7 is added to the aqueous layer, and the mixture is maintained at a temperature of 20°–30° C. On the other hand, 115 g of the filtrate (B) obtained in Example 7 and 115 g of a 70% aqueous nitric acid solution are placed in a dropping funnel and added dropwise to the aforementioned flask. The liquid becomes turbid and turns yellowish white, as soon as the addition is initiated. After the addition is over, the reaction mixture is further maintained at the same temperature for 3 hours. The reaction mixture is cooled to 5° C. and filtered. The product is washed with water and dried to give 2,4-dichloro-3-ethyl-6-nitrophenol.

Yield, 143 g (94% yield based on 4-chloro-3-ethylphenol),

Purity, 99.0% (percentage based on LC area).

EXAMPLE 9

In a 1-liter four-necked glass flask is prepared a solution mixture of 100 g of 4-chloro-3-ethylphenol and 350 g of dichloroethane. While the mixture is maintained at a temperature of 35°–45° C., 80 g of chlorosulfonic acid is added dropwise and the mixture is maintained at a temperature of 40°–45° C. for 1 hour. Next, 326 g of a 14.3% hydrochloric acid solution is added, and 68 g of a 35% aqueous hydrogen peroxide solution is added dropwise while maintaining the temperature at 40°–45° C. After the mixture is maintained at the same temperature for 8 hours, it is cooled to 20° C. After the oily layer is separated, the aqueous layer obtained is charged in a 1-liter four-necked glass flask, and 34.5 g of a 70% nitric acid solution is added dropwise to the aqueous layer at a temperature of 30°–40° C. The liquid becomes turbid and turns yellowish white after 35 minutes from the addition.

The temperature is raised about 3° C. Next, 138 g of a 70% nitric acid solution is added dropwise, and the mixture is maintained at a same temperature for 1 hour. The reaction mixture is cooled to 5° C. and filtered. The product is washed with water and dried to give 2,4-dichloro-3-ethyl-6-nitrophenol.

Yield, 123.5 g (82% yield based on 4-chloro-3 -ethylphenol),

Purity, 95.6% (percentage based on LC area).

EXAMPLE 10

In a 1-liter four-necked glass flask is prepared a solution mixture of 100 g of 4-chloro-3-ethylphenol and 350 g of dichloroethane. While the mixture is maintained at a temperature of 35°–45° C., 80 g of chlorosulfonic acid is added dropwise and the mixture is maintained at a temperature of 40°–45° C. for 1 hour. Next, 326 g of a 14.3% hydrochloric acid solution is added, and 68 g of a 35% aqueous hydrogen peroxide solution is added dropwise while maintaining the temperature at 40°–45° C. After the mixture is maintained at the same temperature for 8 hours, it is cooled to 20° C. After the oily layer is separated, the aqueous layer obtained is charged in a 1-liter four-necked glass flask, and 172 g of a 70% nitric acid solution is added dropwise to the aqueous a temperature of 30°–40° C. The liquid becomes turbid and turns yellowish white. The temperature is raised about 15° C. After the addition, the reaction mixture is maintained at the same temperature for 1 hour. The reaction mixture is cooled to 5° C. and filtered. The product is washed with water and dried to give 2,4-dichloro-3-ethyl-6-nitrophenol.

Yield, 117.5 g (78% yield based on 4-chloro-3-ethylphenol),

Purity, 92.3% (percentage based on LC area).

EXAMPLE 11

In a 1-liter four-necked glass flask is prepared a solution mixture of 100 g of 4-chloro-3-methylphenol and 250 g of dichloromethane. While the mixture is maintained at a temperature of 25°–35° C., 80 g of chlorosulfonic acid is added dropwise. After the mixture is maintained at the same temperature as above for 3 hours, 200 g of water is added dropwise while the reaction mixture is cooled with ice-water.

Next, 133 g of a 35% hydrochloric acid solution is added, and 93 g of a 35% aqueous hydrogen peroxide solution is added dropwise while maintaining the temperature at 30° C. After the mixture is maintained at the same temperature for 8 hours, an aqueous layer is separated from an oily layer. In a 2-liter four-necked glass flask, 115 g of a 70% nitric acid solution is charged, and the aqueous layer separated as above is added dropwise thereto at a temperature of 30°–35° C. After the reaction mixture is maintained at the same temperature for 1 hour, it was cooled to 15° C. and filtered. The product is washed with water and dried to give 2,4-dichloro-3-methyl-6-nitrophenol.

Yield, 125 g (85% yield based on 4-chloro-3-methylphenol),

Melting point, 82°–84° C.

EXAMPLE 12

When the reaction is conducted in the same manner as in Example 1 except that 100 g of 4-chloro-3-isopropylphenol is used as a raw material in place of the 4-chloro-3-ethylphenol, 2,4-dichloro-3-isopropyl-6-nitrophenol is obtained.

Yield, 146.5 g (75% yield based on 4-chloro-3-isopropylphenol),

Melting point, 86°–88° C.

EXAMPLE 13

In a 1-liter four-necked glass flask is prepared a solution mixture of 100 g of 4-chloro-3-ethylphenol and 200 g of monochlorobenzene. While the mixture is maintained at a temperature of 25°–30° C., 80 g of chlorosulfonic acid is added dropwise. After the mixture is maintained at the same temperature for 3 hours, the reaction mass of 5-chloro-4-ethyl-2-hydroxybenzenesulfonic acid is obtained and 75.1 g of acetic acid is added to the reaction mass. After 1.33 g of aluminium chloride and 0.67 g of sulfur chloride are added, 110 g of sulfuryl chloride is added dropwise. After the addition is completed, the temperature of the mixture is raised to 35° C. and the mixture is maintained at the temperature for 5 hours. In a 2-liter flask is charged 960 g of water, and the reaction mass is poured into the flask under stirring. The reaction mixture is separated into an aqueous layer and an oil layer, and the lower oil layer is removed to obtain aqueous solution of 3,5-dichloro-4-ethyl-2-hydroxybenzenesulfonic acid. After cooling to 20° C., 184 g of a 70% nitric acid solution is added dropwise, maintaining the temperature at 20°–25° C. After the addition is completed, the reaction mixture is heated to 45° C. and maintained at the temperature for 4 hours. The reaction mixture is cooled to 20° C. and filtered. The product is washed with water and dried to give 2,4-dichloro-3-ethyl-6-nitrophenol.

Melting point, 46.3°–47.3° C.

Yield, 116 g (77.0% yield based on 4-chloro-3-ethylphenol).

EXAMPLE 14

To the reaction mass of 5-chloro-4-ethyl-2-hydroxybenzenesulfonic acid obtained in the same manner as in Example 13 is added 110 g of water to dissolve the mass, and 48 g of chlorine gas is blown into the solution, maintaining the temperature at 20°–25° C. The mixture is maintained at 25°–30° C. for 5 hours to give 3,5- dichloro-4-ethyl-2-hydroxybenzenesulfonic acid. In the same manner as in Example 13, 2,4-dichloro-3-ethyl-6-nitrophenol is obtained.

Yield, 106.3 g (70.5% yield based on 4-chloro-3-ethylphenol).

EXAMPLE 15

In the same manner as in Example 13 except that 1,2-dichloroethane is used in place of the monochlorobenzene as a solvent, 2,4-dichloro-3-ethyl-6-nitrophenol is obtained.

Yield, 106.9 g (70.9% yield based on 4-chloro-3-ethylphenol).

EXAMPLE 16

In the same manner as in Example 13 except that an aqueous solution of 3,5-dichloro-4-ethyl-2-hydroxybenzenesulfonic acid is added dropwise to a 50% aqueous nitric acid solution which have been preliminarily charged, the aimed product of 2,4-dichloro-3-ethyl-6-nitrophenol is obtained.

Yield, 125.7 g (83.4% yield based on 4-chloro-3-ethylphenol).

We claim:

1. A process for preparing 2,4-dichloro-3-alkyl-6-nitrophenol, comprising:
   (1) sulfonating 4-chloro-3-alkylphenol;
   (2) chlorinating; and (3) nitrating;
   wherein said chlorinating step is effected in an aqueous medium by an aqueous hydrogen chloride solution and an aqueous hydrogen peroxide solution.

2. A process according to claim 1, wherein the aqueous hydrogen chloride solution is a 5%–38% hydrogen chloride solution.

3. A process according to claim 1, wherein the aqueous hydrogen peroxide solution is an aqueous solution of 5%–70% $H_2O_2$.

4. A process according to claim 1, wherein aluminium chloride or ferric chloride is used as a catalyst for the chlorination.

5. A process for preparing 2,4-dichloro-3-alkyl-6-nitrophenol according to claim 1, wherein a 4-chloro-3-$C_1$–$C_4$-alkylphenol is sulfonated with chlorosulfonic acid in an organic solvent to give a 5-chloro-4-$C_1$–$C_4$-alkyl-2-hydroxybenzenesulfonic acid.

6. A process according to claim 5, wherein the organic solvent is selected from a halogenated hydrocarbon, a nitrated hydrocarbon and an aromatic hydrocarbon.

7. A process according to claim 5, wherein an amount of the organic solvent used is 1–10 times by weight as much as the 4-chloro-3-$C_1$–$C_4$-alkylphenol.

8. A process according to claim 5, wherein an amount of the chlorosulfonic acid used is 0.9–1.4 times by weight as much as the 4-chloro-3-$C_1$–$C_4$-alkylphenol.

9. A process for preparing 2,4-dichloro-3-$C_1$–$C_4$-alkyl-6-nitrophenol according to claim 1, wherein the 3,5-dichloro-4-$C_1$–$C_4$-alkyl-2-hydroxybenzenesulfonic acid is added dropwise to an aqueous nitric acid solution in order to substitute the sulfonic acid group with a nitro group.

10. A process according to claim 9, wherein the nitric acid of the aqueous nitric acid solution has a concentration of 2–70% by weight.

11. A process for preparing a 2,4-dichloro-3$C_1$–$C_4$-alkyl-6-nitrophenol according to claim 1, further comprising:
   (4) separating 2,4-dichloro-3-$C_1$–$C_4$-alkyl-6-nitrophenol from the nitrating medium by filtration; wherein at least part of the filtrate or supernatant obtained by said separation of the resulting 2,4-dichloro-3-$C_1$–$C_4$-alkyl-6-nitrophenol is recycled to the nitrating medium.

12. A process for preparing 2,4-dichloro-3-alkyl-6-nitrophenol, comprising:
   (1) sulfonating 4-chloro-3-alkylphenol;
   (2) chlorinating; and (3) nitrating;
   wherein said sulfonating step is effected by chlorosulfonic acid in an organic solvent.

13. A process according to claim 12, wherein the organic solvent is selected from a halogenated hydrocarbon, a nitrated hydrocarbon and an aromatic hydrocarbon.

14. A process according to claims 12 or 13, wherein an amount of the organic solvent used is 1–10 times by weight as much as the 4-chloro-3-alkylphenol.

15. A process according to any one of claim 9, wherein the amount of the chlorosulfonic acid used is 0.9–1.4 times by weight as much as the 4-chloro-3-$C_1$–$C_4$-alkylphenol.

16. A process for preparing a 2,4dichloro-3-$C_1$–$C_4$-alkyl-4-nitrophenol comprising sulfonating a 4-chloro-6-$C_1$–$C_4$-alkylphenol with a sulfonating agent to give a 5-chloro-4-$C_1$–$C_4$-alkyl-2-hydroxybenzenesulfonic acid, chlorinating the sulfonic acid to give a 3,5-dichloro-4-$C_1$–$C_4$-alkyl-2-hydroxybenzenesulfonic acid, and adding dropwise the 3,5-dichloro-4-$C_1$–$C_4$-alkyl-2-hydroxybenzenesulfonic acid in the form of an aqueous solution to an aqueous nitric acid solution until the sulfonic acid group of the sulfonic acid compound is substituted by the nitro group resulting in 2,4-dichloro-3-$C_1$–$C_4$-alkyl-6-nitrophenol.

17. A process for preparing a 2,4-dichloro-3-$C_1$–$C_4$-alkyl-6-nitrophenol by sulfonating a 4-chloro-3-$C_1$–$C_4$-alkylphenol with a sulfonating agent to give a 5-chloro-4-$C_1$–$C_4$-alkyl-2-hydroxybenzenesulfonic acid, chlorinating the sulfonic acid to give a 3,5-dichloro-4-$C_1$–$C_4$-alkyl-2-hydroxybenzenesulfonic acid, substituting the sulfonic acid group in the sulfonic acid by a nitro group with nitric acid, and recycling a filtrate obtained by separation of the resulting 2,4-dichloro-3-$C_1$–$C_4$-alkyl-6-nitrophenol or a supernatant as at least a part of a medium to the substituting step.

18. A process according to claim 12, wherein said 6-chloro-3-alkylphenol is 4-chloro-3-ethylphenol.

19. A process according to claim 16, wherein said aqueous nitric acid solution has a nitric acid concentration of 2–70% by weight.

20. A process for preparing 2,4-dichloro-3-$C_1$–$C_4$-alkyl-6-nitrophenol, comprising:
   (1) sulfonating a 4-chloro-3-$C_1$–$C_4$-alkylphenol to form 5-chloro-4-$C_1$–$C_4$-alkyl-2-hydroxybenzenesulfonic acid;
   (2) chlorinating the sulfonic acid compound produced in (1) so as to form 3,5-dichloro-4-$C_1$–$C_4$-alkyl-2-hydroxybenzenesulfonic acid; and (3) nitrating the sulfonic acid compound formed in (2) with nitric acid so as to substitute a nitro group for the sulfonic acid group and thereby produce 2,4-dichloro-3-$C_1$–$C_4$-alkyl-6-nitrophenol;
   wherein said chlorinating step is carried out by combining in an aqueous medium an aqueous hydrogen chloride solution and an aqueous hydrogen peroxide solution with the sulfonic acid compound produced in step (1).

21. The process according to claim 20, wherein said sulfonating step comprises contacting said 4-chloro-3-$C_1$–$C_4$-alkylphenol with chlorosulfonic acid in an organic solvent.

* * * * *